US009566347B2

(12) United States Patent
Discher et al.

(10) Patent No.: US 9,566,347 B2
(45) Date of Patent: Feb. 14, 2017

(54) PEPTIDES AND METHODS USING SAME

(75) Inventors: Dennis E. Discher, Philadelphia, PA (US); Pia L. Rodriguez Nunez, Philadelphia, PA (US); Diego A. Pantano, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 175 days.

(21) Appl. No.: 13/976,319

(22) PCT Filed: Feb. 7, 2012

(86) PCT No.: PCT/US2012/024174

§ 371 (c)(1), (2), (4) Date: Jan. 6, 2014

(87) PCT Pub. No.: WO2012/109267

PCT Pub. Date: Aug. 16, 2012

(65) Prior Publication Data

US 2014/0140926 A1 May 22, 2014

Related U.S. Application Data

(60) Provisional application No. 61/440,175, filed on Feb. 7, 2011.

(51) Int. Cl.

| | |
|---|---|
| ***A61K 38/00*** | (2006.01) |
| ***C07K 7/06*** | (2006.01) |
| ***A61K 47/48*** | (2006.01) |
| ***C07K 14/705*** | (2006.01) |
| ***A61K 38/17*** | (2006.01) |
| ***C07K 7/08*** | (2006.01) |
| ***C07K 14/00*** | (2006.01) |

(52) U.S. Cl.

CPC ....... *A61K 47/48246* (2013.01); *A61K 38/177* (2013.01); *A61K 47/48853* (2013.01); *C07K 7/06* (2013.01); *C07K 7/08* (2013.01); *C07K 14/001* (2013.01); *C07K 14/70596* (2013.01); *A61K 38/00* (2013.01)

(58) Field of Classification Search

None

See application file for complete search history.

(56) References Cited

U.S. PATENT DOCUMENTS 8,409,653 B2 * 4/2013 Shimono ................... A23J 3/34 426/649
2005/0026847 A1 * 2/2005 Jacobs et al. ................... 514/25
2008/0131431 A1 * 6/2008 Smith et al. ............... 424/134.1
2009/0131453 A1 5/2009 Seal et al.
2010/0070047 A1 3/2010 Smouse
2010/0083253 A1 4/2010 Kushwaha
2010/0316570 A1 * 12/2010 Discher et al. ................ 424/9.1
2012/0024174 A1 2/2012 Sakash et al.

FOREIGN PATENT DOCUMENTS

WO 00/66159 9/2000
WO 2009/131453 10/2009
WO 2010/070047 6/2010
WO 2010/083253 7/2010

OTHER PUBLICATIONS

Barton et. al. Tetrahedron Letters 50 (2009) 2661-2663.*

Cameron et al., "Myxoma Virus M128L is Expressed as a Cell Surface CD47-Like Virulence Factor that Contributes to the Downregulation of Macrophage Activation in Vitro," 2005, *Virology*, 337:55-67.

De Almeida et al., "The Role of Glucocorticoid in SIRPα and SHP-1 Gene Expression in AIHA Patients," 2009, *Immunopharmacology and Immunotoxicology*, 31(4):636-640.

Hatherley et al., "Paired Receptor Specificity Explained by Structures of Signal Regulatory Proteins Alone and Complexed with CD47," 2008, *Molecular Cell*, 31:266-277.

Kinchen et al., "Phagocytic Signaling: You Can Touch, but You Can't Eat," 2008, *Current Biology*, 18(12):R521-R524.

Legrand et al., "Functional CD47/Signal Regulatory Protein Alpha (SIRPα) Interaction is Required for Optimal Human T- and Natural Killer-(NIK) Cell Homeostasis in Vivo," 2011, *PNAS*, 108(32):13224-13229.

Strowig et al., "Transgenic Expression of Human Signal Regulatory Protein alpha in Rag2 $^{-/-}\gamma_c^{-/-}$ Mice Improves Engraftment of Human Hematopoietic Cells in Humanized Mice," 2011, *PNAS*, 108(32):13218-13223.

Tsai et al., "Self Inhibition of Phagocytosis: The Affinity of 'Marker of Self' CD47 for SIRPα Dictates Potency if Inhibition but Only at Low Expression Levels," 2010, *Blood Cells, Molecules, and Diseases*, 45:67-74.

International Search Report for PCT/US12/24174, issued Jul. 27, 2012.

* cited by examiner

*Primary Examiner* — Jeanette Lieb

(74) *Attorney, Agent, or Firm* — Saul Ewing LLP; Kathryn Doyle; Domingos J. Silva

(57) ABSTRACT

The present invention includes a method of modulating the phagocytic activity of at least one phagocyte in a subject. The present invention also includes a method of providing a composition resistant to phagocytosis to a subject. The present invention further includes a method of treating, ameliorating or preventing an inflammatory disease in a subject.

32 Claims, 10 Drawing Sheets

SEQUENCE LISTING

```
<160> NUMBER OF SEQ ID NOS: 4

<210> SEQ ID NO 1
<211> LENGTH: 21
<212> TYPE: PRT
<213> ORGANISM: Artificial Sequence
<220> FEATURE:
<223> OTHER INFORMATION: Chemically synthesized

<400> SEQUENCE: 1

Gly Asn Tyr Thr Cys Glu Val Thr Glu Leu Thr Arg Glu Gly Glu Thr
1               5                   10                  15

Ile Ile Glu Leu Lys
            20


<210> SEQ ID NO 2
<211> LENGTH: 12
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa is selected from the group consisting of
      Cys, Thr and null
<220> FEATURE:
<221> NAME/KEY: MISC_FEATURE
<222> LOCATION: (12)..(12)
<223> OTHER INFORMATION: Xaa is selected from the group consisting of
      Cys, Thr and null

<400> SEQUENCE: 2

Xaa Glu Val Thr Glu Leu Thr Arg Glu Gly Glu Xaa
1               5                   10


<210> SEQ ID NO 3
<211> LENGTH: 10
<212> TYPE: PRT
<213> ORGANISM: Artificial Sequence
<220> FEATURE:
<223> OTHER INFORMATION: Chemically synthesized

<400> SEQUENCE: 3

Glu Val Thr Glu Leu Thr Arg Glu Gly Glu
1               5                   10


<210> SEQ ID NO 4
<211> LENGTH: 12
<212> TYPE: PRT
<213> ORGANISM: Artificial Sequence
<220> FEATURE:
<223> OTHER INFORMATION: Chemically synthesized

<400> SEQUENCE: 4

Cys Glu Val Thr Glu Leu Thr Arg Glu Gly Glu Cys
1               5                   10
```

PEPTIDES AND METHODS USING SAME

CROSS-REFERENCE TO RELATED APPLICATIONS

The present application is a 35 U.S.C. §371 national phase application of, and claims priority to, International Application No. PCT/US12/24174, filed Feb. 7, 2012, and published under PCT Article 21(2) in English, which claims priority under 35 U.S.C. §119(e) to U.S. Provisional Application No. 61/440,175, filed Feb. 7, 2011, all of which applications are hereby incorporated by reference in their entireties herein.

STATEMENT REGARDING FEDERALLY SPONSORED RESEARCH OR DEVELOPMENT

This invention was made with government support under grant number R01 HL062352 by the National Institutes of Health. The government has certain rights in the invention.

BACKGROUND OF THE INVENTION

Phagocytosis is a form of endocytosis wherein solid particles such as bacteria are engulfed by the cell membrane to form an internal phagosome. Phagocytosis is distinct from other forms of endocytosis, such as the vesicular internalization of liquids. Phagocytosis is a key mechanism used by the immune system to remove pathogens, cell debris, dead tissue cells and small mineral particles from circulation in the body.

Phagocytes are white blood cells that protect the body by phagocytosing harmful foreign particles, bacteria, and dead or dying cells, and thus are essential for fighting infections and developing subsequent immunity. Phagocytes of humans and other animals are called "professional" or "non-professional" depending on how effective they are at phagocytosis (Ernst & Stendahl, 2006, *"Phagocytosis of Bacteria and Bacterial Pathogenicity"*, Cambridge University Press: NY, p. 186). The distinguishing factor between professional and non-professional phagocytes is that professional phagocytes (such as neutrophils, monocytes, macrophages, dendritic cells, and mast cells) have surface receptors that can detect harmful objects, such as bacteria, that are not normally found in the body. The immune system recognizes invading cells (such as microbes and viruses) as foreign because these invading cells either express determinants that are absent on host cells or do not express "markers of self" that are normally present on host cells. Injected or implanted materials are also perceived as foreign as these invariably activate macrophages and other phagocytes, and this foreign body response occurs in spite of synthetic coatings such as those with polyethylene glycol (PEG) that are intended to maximize compatibility.

During an infection by a pathogen, chemical signals attract phagocytes to places where the pathogen has invaded the body. These chemical signals may come from bacteria or from other phagocytes already present. When phagocytes come into contact with bacteria, the receptors on the phagocyte's surface bind to them, leading to the engulfing of the bacteria by the phagocyte. Some phagocytes kill the ingested pathogen with oxidants and nitric oxide. After phagocytosis, macrophages and dendritic cells can also participate in antigen presentation, a process in which a phagocyte moves parts of the ingested material back to its surface. The antigen is then displayed to other cells of the immune system. Some phagocytes then travel to the body's lymph nodes and display the material to white blood cells called lymphocytes, a key event in the development of immunity.

Phagocytes are thus professional eating cells of the innate immune system and are responsible for protecting humans and other animals from attacks by foreign pathogens. However, phagocytes may also attack elements that have been intentionally introduced into the body, such as implants, artificial tissue, artificial organs and vesicles bearing therapeutic agents, and this may reduce their lifetime in the body. Furthermore, pathogens have evolved methods to evade attacks by phagocytes, such as covering themselves with molecules that deflect recognition and/or attachment of phagocytes.

A phagocyte may display many types of receptors on its surface, including opsonin receptors, scavenger receptors, and Toll-like receptors. Opsonin receptors increase the phagocytosis of bacteria that have been coated with immunoglobulin G (IgG) antibodies or with complement (a complex series of blood proteins that destroy cells or mark them for destruction). While scavenger receptors bind to a large range of molecules on the surface of bacterial cells, Toll-like receptors bind to more specific molecules, increasing phagocytosis and causing the phagocyte to release inflammatory hormones.

The protein signal regulatory protein-alpha (SIRP-alpha), also known as tyrosine-protein phosphatase non-receptor type substrate 1 or CD172A (cluster of differentiation 172A), is a member of the signal-regulatory-protein (SIRP) family and belongs to the immunoglobulin superfamily. SIRP family members are receptor-type transmembrane glycoproteins known to be involved in the negative regulation of receptor tyrosine kinase-coupled signaling processes.

SIRP-alpha has been shown to be an inhibitory phagocyte receptor. Once it is activated, SIRP-alpha inhibits pro-phagocytic signals from Fc and complement receptors, resulting in inhibition of phagocytosis (de Almeida et al., 2009, Immunopharmacol. Immunotoxicol. 31(4):636-40).

Nanoparticles similar in size to viruses are frequently decorated with antibodies for targeted therapeutics or imaging. Although such particles are sufficiently small to avoid passive entrapment by capillaries in vivo, macrophages in the spleen and liver are well known to clear liposomes and nanoparticles (even when coated with PEG) within hours or days of injection into the circulation. This limits delivery to sites of disease. Whether phagocytosis of antibody-opsonized small particles (<500 nm) involves the same set of signals as larger particles remains a broad research question. A particle that activates SIRP-alpha could in principle limit phagocytic clearance in vivo as well as in vitro and also through help clarify lower size limits for its signaling in phagocytic pathways.

SIRP-alpha is highly polymorphic within both human and mouse (Strowing, et al., 2011, Proc. Natl. Acad. Sci. USA. 108(32):13218-23), with the likely consequence that this minimizes pathogen interactions with SIRP-alpha (Hatherley et al., 2008, Mol Cell 31(2):266-77). Among natural mouse variants, only NOD/SCID mice (and derived strains) express a mouse polymorph of SIRP-alpha that cross-reacts with human cells. This fact may explain why human blood cells engraft and circulate in these mice better than other strains of mice (Strowing, et al., 2011, Proc. Natl. Acad. Sci. USA. 108(32):13218-23; Legrand et al., 2011, Proc. Natl. Acad. Sci. USA. 108(32):13224-9). NSG mice thus provide an ideal platform for in vivo assessment of SIRP-alpha binding and activating ligands on synthetic particles.

There remains a need in the art to identify a novel method for controlling the activity of phagocytes and their interactions with foreign bodies. Such method should allow the labeling of foreign bodies with one or more molecules that would preclude or delay their recognition as foreign by phagocytes. This method would thus ensure that the labeled foreign body is not subjected to immediate phagocytosis and degradation once introduced in the body. The present invention fulfills these needs.

BRIEF SUMMARY OF THE INVENTION

The invention includes a composition comprising compound (I) or a salt thereof, wherein compound (I) comprises a peptide having at least 85% homology with the peptide of SEQ ID NO:2.

In one embodiment, compound (I) comprises a peptide having at least 85% homology with the peptide of SEQ ID NO:3. In another embodiment, compound (I) comprises a peptide having at least 85% homology with the peptide of SEQ ID NO:4. In yet another embodiment, compound (I) comprises a peptide having at least 85% homology with the peptide of SEQ ID NO: 1. In yet another embodiment, compound (I) comprises a peptide having at least 90% homology with the peptide of SEQ ID NO:2. In yet another embodiment, compound (I) comprises a peptide having at least 95% homology with the peptide of SEQ ID NO:2. In yet another embodiment, compound (I) comprises the peptide of SEQ ID NO:2. In yet another embodiment, compound (I) comprises a peptide having at least 95% homology with the peptide of SEQ ID NO:1. In yet another embodiment, compound (I) comprises the peptide of SEQ ID NO:1.

The invention also includes a composition comprising:

compound (II) or a salt thereof:

(II)

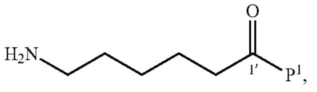

compound (III) or a salt thereof:

(III)

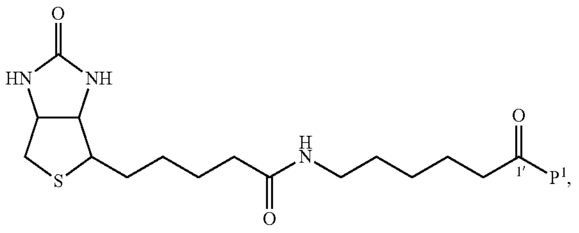

compound (IV) or a salt thereof:

(IV)

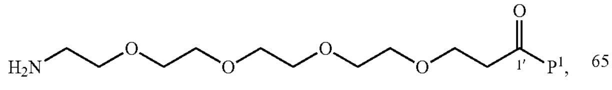

or compound (V) or a salt thereof:

(V)

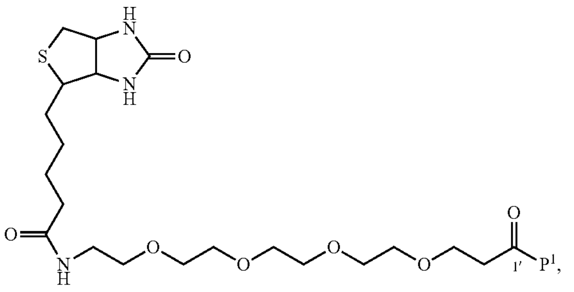

or a salt thereof, wherein $P^1$ comprises a peptide having at least 85% homology with the peptide of SEQ ID NO:2, and $P^1$ is covalently bound through its N-amino terminus via an amide bond to the carbonyl group (1').

In one embodiment, $P^1$ comprises a peptide having at least 85% homology with the peptide of SEQ ID NO:3. In another embodiment, $P^1$ comprises a peptide having at least 85% homology with the peptide of SEQ ID NO:4. In yet another embodiment, $P^1$ comprises a peptide having at least 85% homology with the peptide of SEQ ID NO:1.

The invention also includes a composition comprising a peptide-containing moiety comprising a compound selected from the group consisting of compounds (I)-(V), wherein the peptide-containing moiety is attached to the surface of a solid particle.

In one embodiment, the solid particle is selected from the group consisting of a nanoparticle, vesicle, dendrimer, engineered cell, tissue fragment, implant, and combinations thereof. In another embodiment, the composition further comprises an agent selected from the group consisting of a therapeutic agent, imaging agent, radioactive agent, salt, protein, nucleic acid, gas, and combinations thereof, wherein the agent is attached to or contained within the solid particle. In yet another embodiment, the peptide-containing moiety is attached to the surface of the solid particle by a covalent or non-covalent bond.

The invention also includes a method of modulating phagocytic activity of at least one phagocyte in a subject. The method comprises administering to the subject a pharmaceutical composition comprising a pharmaceutically effective amount of a peptide-containing moiety, wherein the peptide-containing moiety comprises a compound selected from the group consisting of compounds (I)-(V), whereby administering the composition to the subject modulates phagocytic activity of the at least one phagocyte in the subject.

In one embodiment, the composition further comprises a solid particle, wherein the peptide-containing moiety is attached to the surface of the solid particle. In another embodiment, the solid particle is selected from the group consisting of a nanoparticle, vesicle, dendrimer, engineered cell, tissue fragment, implant, and combinations thereof. In yet another embodiment, the composition further comprises an agent selected from the group consisting of a therapeutic agent, imaging agent, radioactive agent, salt, protein, nucleic acid, gas, and combinations thereof, wherein the agent is attached to or contained within the solid particle. In yet another embodiment, the composition further comprises a conjugated compound covalently linked to the peptide-containing moiety. In yet another embodiment, the conjugated compound is selected from the group consisting of a peptide, protein, nucleic acid, lipid, biologically active molecule, and combinations thereof.

The invention also includes a method of providing to a subject a peptide-containing moiety that is resistant to phagocytosis in the subject. The method comprises administering to or introducing into the subject a pharmaceutical composition comprising the peptide-containing moiety, wherein the peptide-containing moiety comprises a compound selected from the group consisting of compounds (I)-(V), whereby the peptide-containing moiety is resistant to phagocytosis in the subject.

In one embodiment, the composition further comprises a solid particle, wherein the peptide-containing moiety is attached to the surface of the solid particle. In another embodiment, the solid particle is selected from the group consisting of a nanoparticle, vesicle, dendrimer, engineered cell, tissue fragment, implant, and combinations thereof. In yet another embodiment, the composition further comprises an agent selected from the group consisting of a therapeutic agent, imaging agent, radioactive agent, salt, protein, nucleic acid, gas and combinations thereof, wherein the agent is attached to or contained within the solid particle. In yet another embodiment, the composition further comprises a conjugated compound covalently linked to the peptide-containing moiety. In yet another embodiment, the conjugated compound is selected from the group consisting of a peptide, protein, nucleic acid, lipid, biologically active molecule, and combinations thereof.

The invention also includes a method of treating, ameliorating or preventing an inflammatory disease in a subject. The method comprises administering to the subject a pharmaceutical composition comprising a pharmaceutically effective amount of a peptide-containing moiety, wherein the peptide-containing moiety comprises a compound selected from the group consisting of compounds (I)-(V), whereby administering the composition to the subject treats, ameliorates or prevents the inflammatory disease in the subject.

In one embodiment, the composition further comprises a solid particle, wherein the peptide-containing moiety is attached to the surface of the solid particle. In another embodiment, the solid particle is selected from the group consisting of a nanoparticle, vesicle, dendrimer, engineered cell, tissue fragment, implant, and combinations thereof. In yet another embodiment, the composition further comprises an agent selected from the group consisting of a therapeutic agent, imaging agent, radioactive agent, salt, protein, nucleic acid, gas, and combinations thereof, wherein the agent is attached to or contained within the solid particle. In yet another embodiment, the composition further comprises a conjugated compound covalently linked to the peptide-containing moiety. In yet another embodiment, the conjugated compound is selected from the group consisting of a peptide, protein, nucleic acid, lipid, biologically active molecule, and combinations thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 3, comprising FIG. 3A illustrates a two color experiment in which nanoparticles (or cells) are mixed and injected into the same mouse after labeling with or without the peptide with distinct fluorescent red dye (PKH26) or far-red (DiD). 50 μl of blood was periodically sampled from the eyes, and flow cytometry analysis of the decay in nanoparticle (or cell) numbers was used to calculate the time-dependent 'persistence ratio' in each mouse. Colors were labeled as 1 and 2. FIG. 3B is a graph illustrating an experiment where 160 nm polystyrene beads coated with streptavidin were bound to biotinylated versions of synthetic FG-peptide, or else negative controls of either scrambled peptide or PEG. Beads were opsonized with anti-streptavidin and then injected. n=6 mice. FIG. 3C is a graph illustrating the inverse correlation between the in vivo ratio of beads with or without peptide at 35 min and the inhibition of phagocytosis in vitro at 45 min for 160 nm beads. FIG. 3D is a graph illustrating macrophage SIRPa1 tyrosine phosphorylation upon contact with FG-peptide bound to opsonized beads and phagocytosed by THP-1 cells. From cell lysates, SIRP-alpha was immunoprecipitated and immunoblotted for quantitation of phosphotyrosine per total SIRP-alpha (n=3). Avg.±SEM for all results.

FIG. 5, comprising FIG. 5A: After about 5 weeks, the tumor-bearing mice received tail vein injection of the mixture of NIR dye-coated beads. Representative picture of Right tumor area Fluorescent intensity at 1 min and 120 min using IVIS Spectrum Imaging System for Opsonized and FG peptide-Opsonized coated 320 nm Streptavidin polystyrene beads. FIG. 5B: Nanoparticles intensities on tumor area fit 1$^{st}$ order kinetics and the values were compared with the ones found for harvesting tumors. FIG. 5C: Tumor harvested average values obtained for each condition. Data are the mean of 2 or 4 tumor ±SEM.

DETAILED DESCRIPTION OF THE INVENTION

Figure 1:
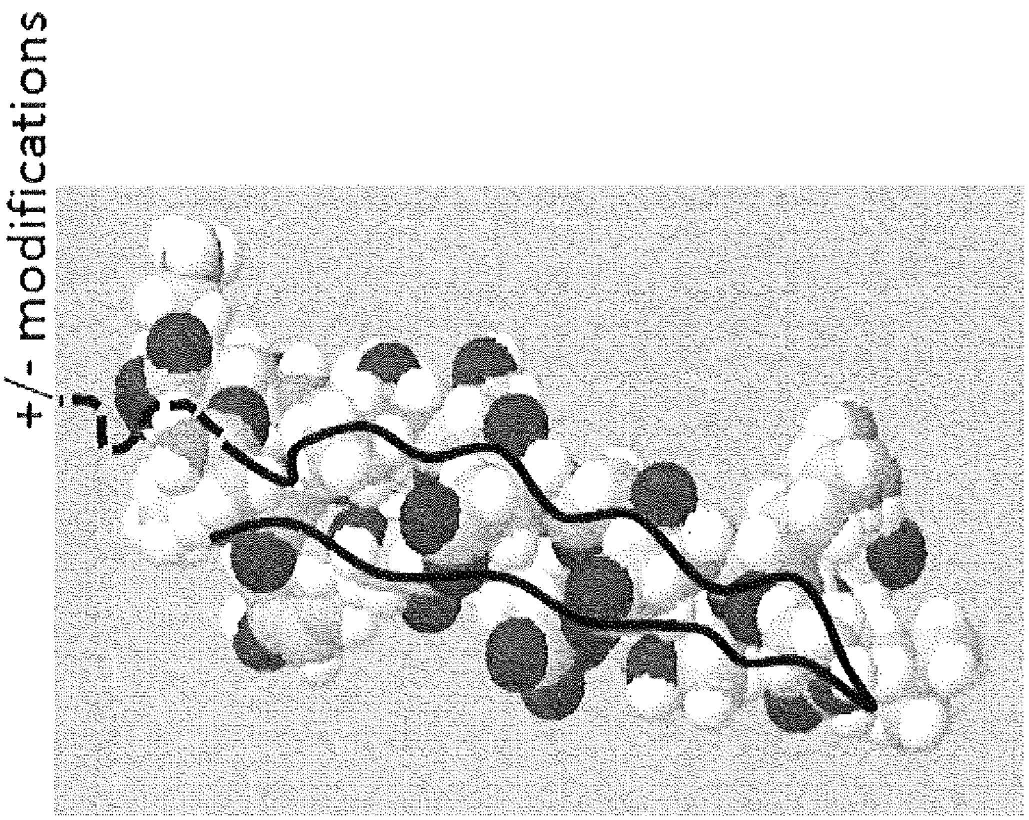
FIG. 1 is a schematic illustration of the computer-based design of synthetic peptides that may bind to SIRP-alpha.

The present invention relates to the unexpected discovery that particles coated with the compounds of the invention undergo reduced or undetectable phagocytosis once introduced into a subject, as compared to equivalent particles that are not coated with the compounds of the invention. In a non-limiting aspect, the peptides of the invention bind to SIRP-alpha receptor on the surface of phagocytes and inhibit the phagocytosis process. The invention described herein represents a novel paradigm for preparing materials that do not undergo phagocytosis once introduced into a subject. The invention also represents a novel approach of controlling the phagocytic activity of phagocytes in a subject.

The results described herein constitute the first example of a synthetic peptide that binds and signals to phagocyte receptors, thereby passivating phagocytes and improving compatibility.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

The articles "a" and "an" are used herein to refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or +10%, more preferably ±5%, even more preferably ±1%, and still more preferably ±0.1% from the specified value, as such variations are appropriate to perform the disclosed methods.

As used herein, the term "RBC" refers to red blood cell.

As used herein, the term "SIRP-a" or "SIRP-α" or "SIRP-alpha" refers to signal regulatory protein-a (also known as signal regulatory protein-a).

As used herein, the term "FG-peptide" refers to the peptide of SEQ ID NO:1 (GNYTCEVTELTREGETIIELK) or a salt thereof.

As used herein, the terms "protein", "peptide" and "polypeptide" are used interchangeably, and refer to a compound comprised of amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Proteins" include, for example, biologically active fragments, substantially homologous proteins, oligopeptides, homodimers, heterodimers, variants of proteins, modified proteins, derivatives, analogs, and fusion proteins, among others. The proteins include natural proteins, recombinant proteins, synthetic proteins, or a combination thereof. A protein may be a receptor or a non-receptor.

As used herein, amino acids are represented by the full name thereof, by the three-letter code as well as the one-letter code corresponding thereto:

| Full Name | 3 Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "fragment," as applied to a protein or peptide, refers to a subsequence of a larger protein or peptide. A "fragment" of a protein or peptide may be at least about 10 amino acids in length; for example, at least about 50 amino acids in length; more preferably, at least about 100 amino acids in length; even more preferably, at least about 200 amino acids in length; particularly preferably, at least about 300 amino acids in length; and most preferably, at least about 400 amino acids in length.

As used herein, a "nucleic acid" refers to a polynucleotide and includes polyribonucleotides and polydeoxyribonucleotides.

As used herein, the term "homologous" refers to the subunit sequence similarity between two polymeric molecules, e.g., between two nucleic acid molecules, such as two DNA molecules or two RNA molecules, or between two protein molecules. When a subunit position in both of the two molecules is occupied by the same monomeric subunit; e.g., if a position in each of two DNA molecules is occupied by adenine, they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. By way of example, the DNA sequences 3'ATTGCC5' and 3'TATGGC5' are 50% homologous. As used herein, "homology" is used synonymously with "identity."

As used herein, the term "substantially the same" amino acid sequence is defined as a sequence with at least 70%, preferably at least about 80%, more preferably at least about 85%, more preferably at least about 90%, even more preferably at least about 95%, and most preferably at least 99% homology with another amino acid sequence, as determined by the FASTA search method in accordance with Pearson & Lipman, 1988, Proc. Natl. Inst. Acad. Sci. USA 85:2444-48.

By the term "specifically bind" or "specifically binds," as used herein, is meant that a first molecule (e.g., an antibody) preferentially binds to a second molecule (e.g., a particular antigenic epitope), but does not necessarily bind only to that second molecule.

"Isolated" means altered or removed from the natural state through the actions of a human being. For example, a nucleic acid or a protein naturally present in a living animal is not "isolated," but the same nucleic acid or protein partially or completely separated from the coexisting materials of its natural state is "isolated." An isolated nucleic acid or protein can exist in substantially purified form, or can exist in a non-native environment such as, for example, a host cell.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the terms "effective amount" and "pharmaceutically effective amount" refer to a nontoxic but sufficient amount of an agent or drug to provide the desired biological result. That result can be reduction and/or alleviation of the signs, symptoms, or causes of a disease or disorder, imaging or monitoring of an in vitro or in vivo system (including a living organism), or any other desired alteration of a biological system. An appropriate effective amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions of the Invention

The invention includes a composition comprising compound (I) or a salt thereof, wherein the compound (I) comprises a peptide having at least 85% homology with the peptide of SEQ ID NO:2 (Xaa-EVTELTREGE-Xaa), wherein each occurrence of Xaa is independently selected from the group consisting of C, T and null. In one embodiment, when both occurrences of Xaa are C, the two cysteine residues may exist in a cyclic disulfide-linked form (i.e., form a cyclic intramolecular cystine form). Both the noncyclic cysteine form of peptide of SEQ ID NO:2 and the cyclic cystine form of SEQ ID NO:2 are contemplated within the invention.

In one embodiment, the compound (I) comprises a peptide having at least 85% homology with the peptide of SEQ ID NO:3 (EVTELTREGE). In another embodiment, the compound (I) comprises a peptide having at least 85% homology with the peptide of SEQ ID NO:4 (CEVTELTREGEC). In yet another embodiment, the compound (I) comprises a peptide having at least 85% homology with the peptide of SEQ ID NO:1 (GNYTCEVTELTREGETIIELK).

In one embodiment, the compound (I) comprises a peptide having at least 90% homology with the peptide of SEQ ID NO:2 or a salt thereof. In another embodiment, the compound (I) comprises a peptide having at least 95% homology with the peptide of SEQ ID NO:2 or a salt thereof. In yet another embodiment, the compound (I) comprises the peptide of SEQ ID NO:2 or a salt thereof. In yet another embodiment, the compound (I) consists of the peptide of SEQ ID NO:2 or a salt thereof.

In one embodiment, the compound (I) comprises a peptide having at least 90% homology with the peptide of SEQ ID NO:3 or a salt thereof. In another embodiment, the compound (I) comprises a peptide having at least 95% homology with the peptide of SEQ ID NO:3 or a salt thereof. In yet another embodiment, the compound (I) comprises the peptide of SEQ ID NO:3 or a salt thereof. In yet another embodiment, the compound (I) consists of the peptide of SEQ ID NO:3 or a salt thereof.

In one embodiment, the compound (I) comprises a peptide having at least 90% homology with the peptide of SEQ ID NO:4 or a salt thereof. In another embodiment, the compound (I) comprises a peptide having at least 95% homology with the peptide of SEQ ID NO:4 or a salt thereof. In yet another embodiment, the compound (I) comprises the peptide of SEQ ID NO:4 or a salt thereof. In yet another embodiment, the compound (I) consists of the peptide of SEQ ID NO:4 or a salt thereof.

In one embodiment, the compound (I) comprises a peptide having at least 90% homology with the peptide of SEQ ID NO:1 or a salt thereof. In another embodiment, the compound (I) comprises a peptide having at least 95% homology with the peptide of SEQ ID NO:1 or a salt thereof. In yet another embodiment, the compound (I) comprises the peptide of SEQ ID NO:1 or a salt thereof. In yet another embodiment, the compound (I) consists of the peptide of SEQ ID NO:1 or a salt thereof.

The invention also includes a composition comprising compound (II):

(II)

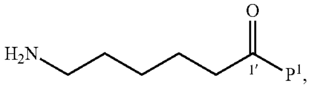

or a salt thereof, wherein $P^1$ comprises a peptide having at least 85% homology with the peptide of SEQ ID NO:2, wherein $P^1$ is covalently bound through its N-amino terminus via an amide bond to the carbonyl group (1').

In one embodiment, $P^1$ comprises a peptide having at least 85% homology with the peptide of SEQ ID NO:3 (EVTELTREGE). In another embodiment, $P^1$ comprises a peptide having at least 85% homology with the peptide of SEQ ID NO:4 (CEVTELTREGEC). In yet another embodiment, $P^1$ comprises a peptide having at least 85% homology with the peptide of SEQ ID NO:1 (GNYTCEVTELTREGETIIELK).

In one embodiment, $P^1$ comprises a peptide having at least 90% homology with the peptide of SEQ ID NO:2 or a salt thereof. In another embodiment, $P^1$ comprises a peptide having at least 95% homology with the peptide of SEQ ID NO:2 or a salt thereof. In yet another embodiment, $P^1$ comprises the peptide of SEQ ID NO:2 or a salt thereof. In yet another embodiment, $P^1$ consists of the peptide of SEQ ID NO:2 or a salt thereof.

In one embodiment, $P^1$ comprises a peptide having at least 90% homology with the peptide of SEQ ID NO:3 or a salt thereof. In another embodiment, $P^1$ comprises a peptide having at least 95% homology with the peptide of SEQ ID NO:3 or a salt thereof. In yet another embodiment, $P^1$ comprises the peptide of SEQ ID NO:3 or a salt thereof. In yet another embodiment, $P^1$ consists of the peptide of SEQ ID NO:3 or a salt thereof.

In one embodiment, $P^1$ comprises a peptide having at least 90% homology with the peptide of SEQ ID NO:4 or a salt thereof. In another embodiment, $P^1$ comprises a peptide having at least 95% homology with the peptide of SEQ ID NO:4 or a salt thereof. In yet another embodiment, $P^1$ comprises the peptide of SEQ ID NO:4 or a salt thereof. In yet another embodiment, $P^1$ consists of the peptide of SEQ ID NO:4 or a salt thereof.

In one embodiment, $P^1$ comprises a peptide having at least 90% homology with the peptide of SEQ ID NO:1 or a salt thereof. In another embodiment, $P^1$ comprises a peptide having at least 95% homology with the peptide of SEQ ID NO:1 or a salt thereof. In yet another embodiment, $P^1$ comprises the peptide of SEQ ID NO:1 or a salt thereof. In yet another embodiment, $P^1$ consists of the peptide of SEQ ID NO:1 or a salt thereof.

The invention further includes a composition comprising compound (III):

(III)

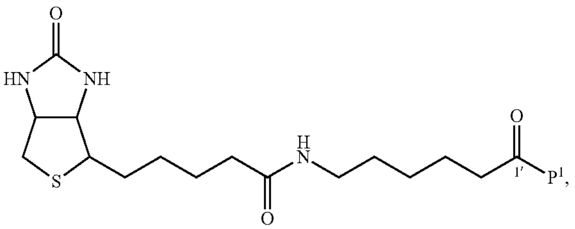

or a salt thereof, wherein $P^1$ comprises a peptide having at least 85% homology with the peptide of SEQ ID NO:2, wherein $P^1$ is covalently bound through its N-amino terminus via an amide bond to the carbonyl group (1').

The invention also includes a composition comprising compound (IV):

(IV)

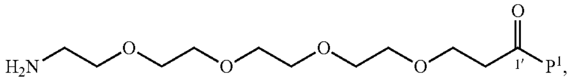

or a salt thereof, wherein $P^1$ comprises a peptide having at least 85% homology with the peptide of SEQ ID NO:2, wherein $P^1$ is covalently bound through its N-amino terminus via an amide bond to the carbonyl group (1').

The invention also includes a composition comprising compound (V):

(V)

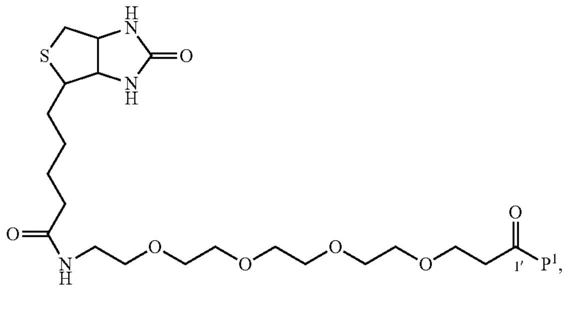

or a salt thereof, wherein $P^1$ comprises a peptide having at least 85% homology with the peptide of SEQ ID NO:2, wherein $P^1$ is covalently bound through its N-amino terminus via an amide bond to the carbonyl group (1').

In one embodiment, $P^1$ comprises a peptide having 90% homology with the peptide of SEQ ID NO:2 or a salt thereof. In another embodiment, $P^1$ comprises a peptide having at least 95% homology with the peptide of SEQ ID NO:2 or a salt thereof. In yet another embodiment, $P^1$ comprises the peptide of SEQ ID NO:2 or a salt thereof. In yet another embodiment, $P^1$ consists of the peptide of SEQ ID NO:2 or a salt thereof.

The invention further includes a composition comprising a peptide-containing moiety, wherein the peptide-containing moiety comprises a compound selected from the group consisting of compounds (I)-(V), and the peptide-containing moiety is attached to the surface of a solid particle.

In one embodiment, the solid particle is selected from the group consisting of a nanoparticle, vesicle, dendrimer, engineered cell, tissue fragment, implant, and combinations thereof. In another embodiment, the composition further comprises an agent selected from the group consisting of a therapeutic agent, imaging agent, radioactive agent, salt, protein, nucleic acid, gas, and combinations thereof, wherein the agent is attached to or contained within the solid particle. In yet another embodiment, the peptide-containing moiety is attached to the surface of the solid particle by a covalent or non-covalent bond.

In one embodiment, the peptide-containing moiety is attached to the whole surface of the solid particle. In another embodiment, the peptide-containing moiety is attached to at least a fraction of the surface of the solid particle.

Preparation of the Compositions of the Invention

Compounds (I)-(V) or a salt thereof may be synthesized using chemical and biochemical methods known to those skilled in the art of chemical synthesis or peptide synthesis.

Compounds (I)-(V) may be attached to the surface of a solid particle using any method known to those skilled in the art. In one embodiment, compounds (I)-(V) may be attached to the surface of a solid particle via a covalent bond. In a non-limiting example, a free amino group in compound (I), (H) or (IV) may be attached to free carboxylate groups on the surface of a solid particle via covalent amide bonds. In another embodiment, compounds (I)-(V) may be attached to the surface of a solid particle via a non-covalent bond. In a non-limiting example, the free biotin in compound (III) or (V) may form a tight non-covalent bond with free avidin molecules immobilized on the surface of a solid particle.

The solid particles useful within the invention include, but are not limited to, a nanoparticle, vesicle, dendrimer, engineered cell, tissue fragment, or implant. The particles may be prepared using methods known to those skilled in the art or purchased from commercial sources.

Methods of the Invention

The invention includes a method of modulating the phagocytic activity of at least one phagocyte in a subject. The method comprises administering to the subject a pharmaceutical composition comprising a pharmaceutically effective amount of a peptide-containing moiety, wherein the peptide-containing moiety comprises a compound selected from the group consisting of compounds (I)-(V), whereby administering the composition to the subject modulates the phagocytic activity of the at least one phagocyte in the subject.

In one embodiment, the composition further comprises a solid particle, wherein the peptide-containing moiety is attached to the surface of the solid particle. In another embodiment, the solid particle is selected from the group consisting of a nanoparticle, vesicle, dendrimer, engineered cell, tissue fragment, implant, and combinations thereof. In another embodiment, the composition further comprises an agent selected from the group consisting of a therapeutic agent, imaging agent, radioactive agent, salt, protein, nucleic acid, gas, and combinations thereof, wherein the agent is attached to or contained within the solid particle. In yet another embodiment, the composition further comprises a conjugated compound, wherein the conjugated compound is covalently linked to the peptide-containing moiety. In yet another embodiment, the conjugated compound is selected from the group consisting of a peptide, protein, nucleic acid, lipid, biologically active molecule, and combinations thereof.

The invention also includes a method of providing to a subject a peptide-containing moiety which is resistant to phagocytosis. The method comprises administering to or introducing into the subject a pharmaceutical composition comprising the peptide-containing moiety, wherein the peptide-containing moiety comprises a compound selected from the group consisting of compounds (I)-(V), whereby the peptide-containing moiety is resistant to phagocytosis in the subject.

In one embodiment, the composition further comprises a solid particle, wherein the peptide-containing moiety is attached to the surface of the solid particle. In another embodiment, the solid particle is selected from the group consisting of a nanoparticle, vesicle, dendrimer, engineered cell, tissue fragment, and implant. In another embodiment, the composition further comprises an agent selected from the group consisting of a therapeutic agent, imaging agent, radioactive agent, salt, protein, nucleic acid, gas, and combinations thereof, wherein the agent is attached to or contained within the solid particle. In yet another embodiment, the composition further comprises a conjugated compound, wherein the conjugated compound is covalently linked to the peptide-containing moiety. In yet another embodiment, the conjugated compound is selected from the group consisting of a peptide, protein, nucleic acid, lipid, biologically active molecule, and combinations thereof.

The invention further includes a method of treating, ameliorating or preventing an inflammatory disease or condition in a subject. The method comprises administering to the subject a pharmaceutical composition comprising a pharmaceutically effective amount of a peptide-containing moiety, wherein the peptide-containing moiety comprises a compound selected from the group consisting of compounds (I)-(V), whereby administering the composition to the subject treats, ameliorates or prevents the inflammatory disease or condition in the subject.

In one embodiment, the composition further comprises a solid particle, wherein the peptide-containing moiety is attached to the surface of the solid particle. In another embodiment, the solid particle is selected from the group consisting of a nanoparticle, vesicle, dendrimer, engineered cell, tissue fragment, implant, and combinations thereof. In another embodiment, the composition further comprises an agent selected from the group consisting of a therapeutic agent, imaging agent, radioactive agent, salt, protein, nucleic acid, gas, and combinations thereof, wherein the agent is attached to or contained within the solid particle. In yet another embodiment, the composition further comprises a conjugated compound, wherein the conjugated compound is covalently linked to the peptide-containing moiety. In yet another embodiment, the conjugated compound is selected from the group consisting of a peptide, protein, nucleic acid, lipid, biologically active molecule, and combinations thereof.

Pharmaceutical Compositions and Formulations

The invention also encompasses the use of pharmaceutical compositions of the invention or salts thereof to practice the methods of the invention. Such a pharmaceutical composition may consist of at least one compound or conjugate of the invention or a salt thereof in a form suitable for administration to a subject, or the pharmaceutical composition may comprise at least one compound or conjugate of the invention or a salt thereof, and one or more pharmaceutically acceptable carriers, one or more additional ingredients, or some combination of these. The compound or conjugate of the invention may be present in the pharmaceutical composition in the form of a physiologically acceptable salt, such as in combination with a physiologically acceptable cation or anion, as is well known in the art.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, vagina or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Routes of Administration

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Coloreon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Vaginal Administration

A pharmaceutical composition of the invention may be prepared, packaged, or sold in a formulation suitable for vaginal administration. With respect to the vaginal or perivaginal administration of the compounds of the invention, dosage forms may include vaginal suppositories, creams, ointments, liquid formulations, pessaries, tampons, gels, pastes, foams or sprays. The suppository, solution, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology, using for example proteins equipped with pH sensitive domains or protease-cleavable fragments. In some eases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to, reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Unless otherwise noted, all starting materials and reagents were obtained from commercial suppliers and used without purification.

Example 1

Circulation Time of Derivatized Beads

Figure 2:
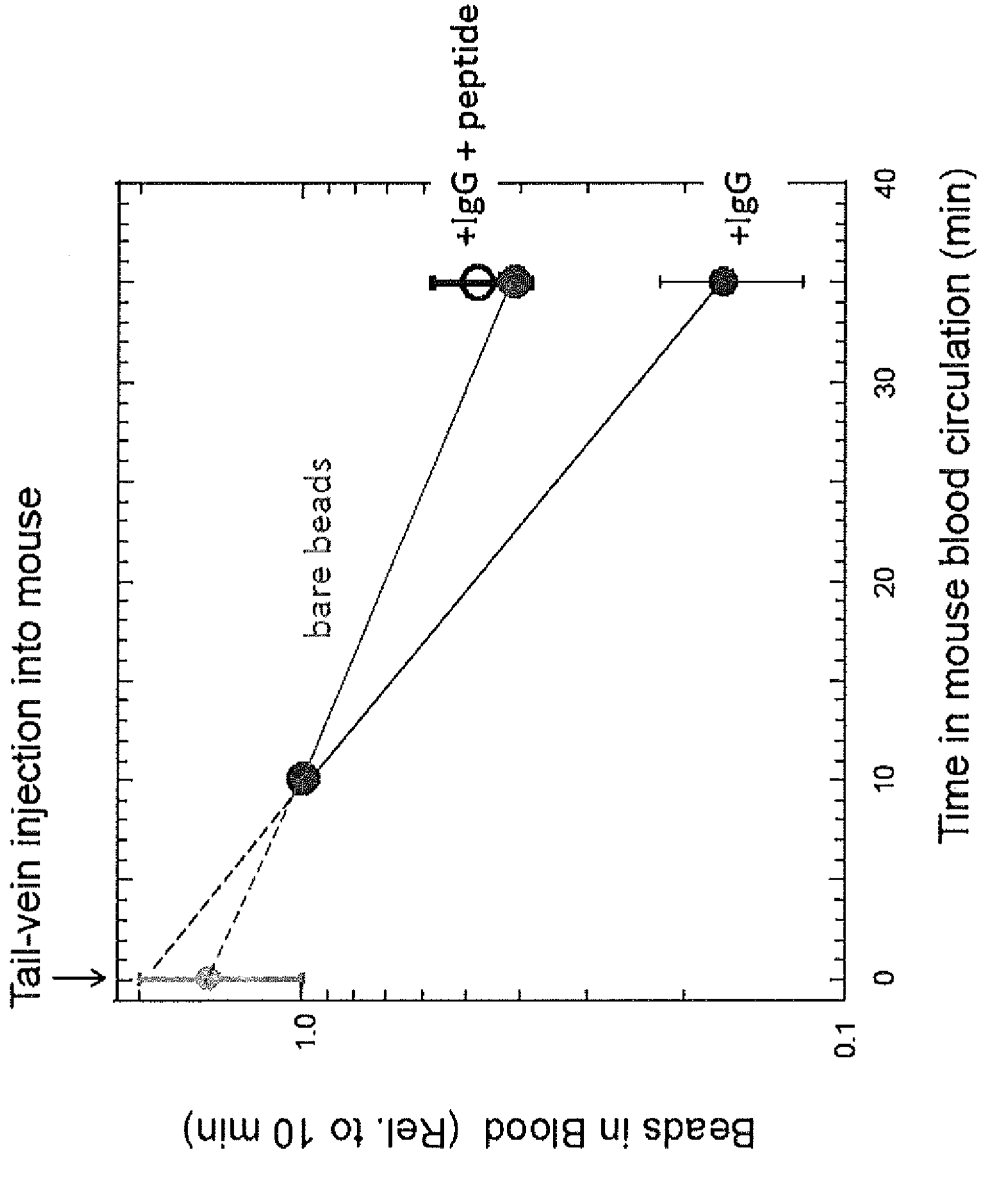
FIG. 2 is a graph illustrating the relative amount of circulating beads in mouse blood as a function of time. The graph illustrates measurements for bare beads, IgG-opsonized beads, and IgG-opsonized beads derivatized with the peptide of SEQ ID NO:1 ("FG-peptide"; GNYTCEVTELTREGETIIELK). The beads were administered by injection into the tail vein of the mouse. For the purpose of comparison, in each experiment the blood concentration of the beads was normalized as 1 at t=10 minutes.

In order to evaluate the effect of compounds of the invention on the blood clearance rate of derivatized beads, parallel experiments were performed wherein a suspension of beads was injected in the tail vein of mice and the blood concentration of the beads in the mice was followed as a function of time (FIG. 2). The beads used in this study were underivatized beads, IgG-opsonized beads, and IgG-opsonized beads derivatized with the peptide of SEQ ID NO:1.

The beads opsonized with IgG had higher clearance rates than underivatized beads, suggesting that the IgG-opsonized beads underwent phagocytosis at higher rates than underivatized beads. IgG-opsonized beads derivatized with the peptide of SEQ ID NO:1 were found to have lower clearance rates than IgG-opsonized beads, and this observation was consistent with the inhibition of phagocytosis by the compounds of the invention.

Example 2

In Vivo Persistence and In Vitro Phagocytosis

To assess whether the particles had been taken up by spleen macrophages in NSG mice, tissue sections were immunostained for macrophages and imaged by fluorescence microscopy. Whole organ imaging of the near-infrared particles continued uptake, with peptide reducing but not eliminating uptake.

Nanoparticles are not sufficiently large or dense to settle in culture, which limit bead contact with cells. However, since binding is a surface-based process, opsonized nanobeads that were added at the same total surface area as micro-beads (rather than the same total particle number) were taken up just as efficiently in culture by macrophages.

Example 3

Minimal Peptide Designs

Three versions of the peptide were designed and simulated by Molecular Dynamics (FIG. 4): (i) the 21-aa FG-peptide of sequence GNYTCEVTELTREGETIIELK (SEQ ID NO:1) that was shown functional above, (ii) a 12-aa FG-SS-peptide with sequence CEVTELTREGEC (SEQ ID NO:4) with a Cys substitution opposite in the hairpin to Cys intended to disulfide-stabilize the β-hairpin; and (iii) a 10-aa FG-hairpin of sequence EVTELTREGE (SEQ ID NO:3) centered on the interacting loop. Equilibration of the three designs respectively indicated: (i) the FG-peptide stably maintains the β-hairpin and an appropriate distribution of surface charge, (ii) the FG-SS-peptide underwent a large torsional distortion that alters the surface charge distribution, and (iii) the short FG-hairpin completely lost the initial hairpin structure.

Figure 3A:
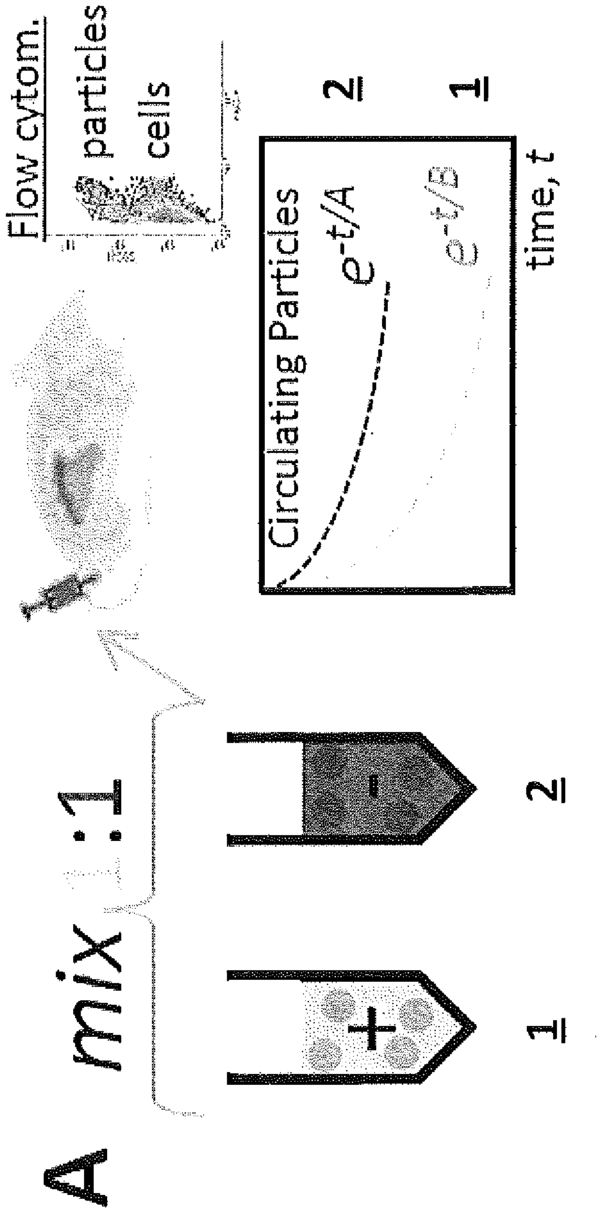
FIGS. 3A-3D, illustrates the finding that FG-peptide prolong the circulation of nanoparticles in NSG mice, correlating inversely with phagocytosis in vitro and with signaling through SIRP-alpha.
Figure 3B:
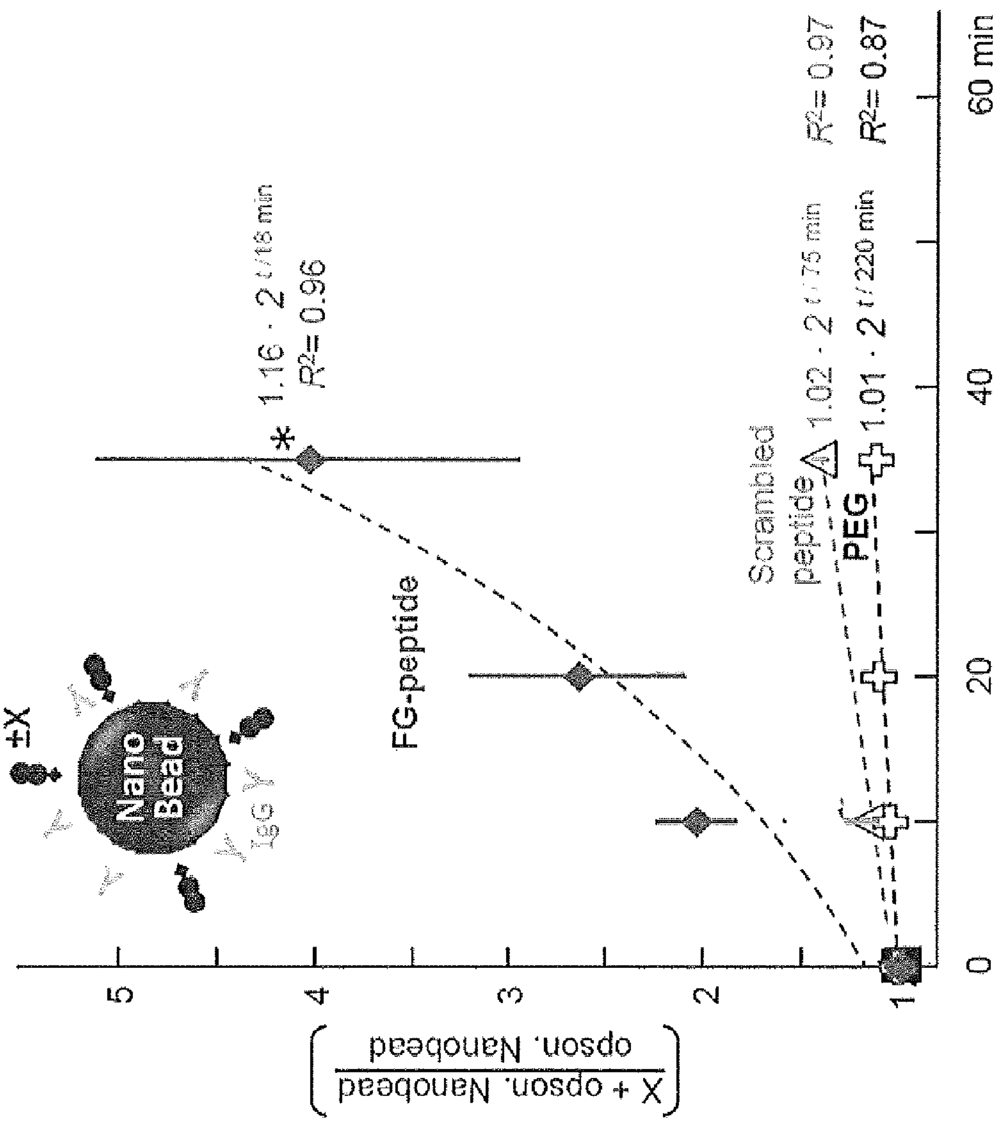
Figure 3C:
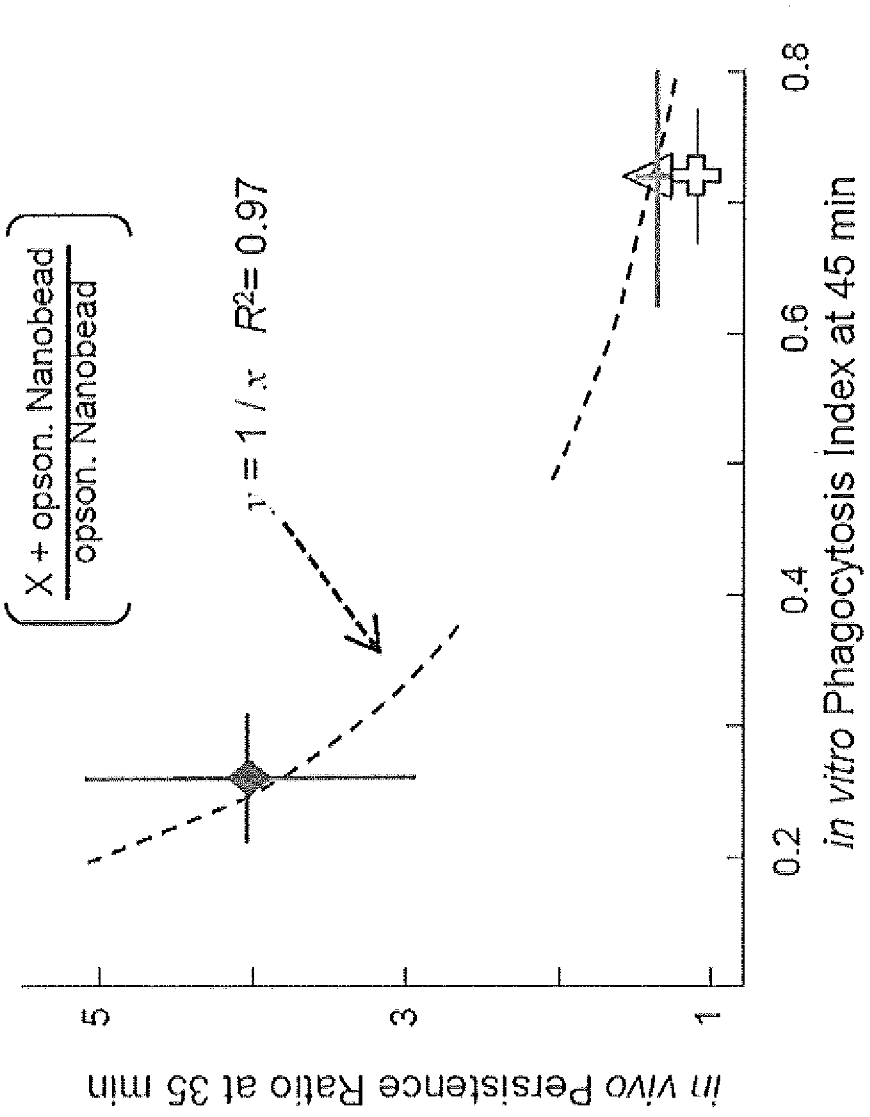
Figure 3D:
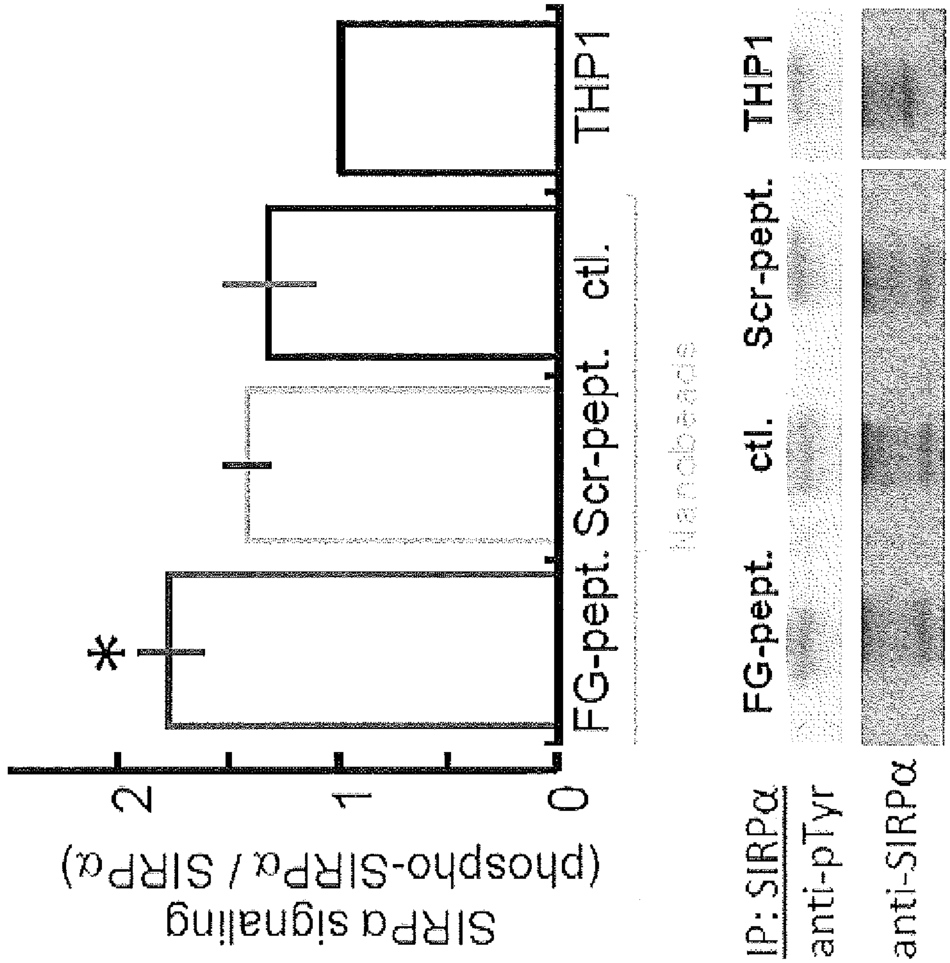
Figure 4:
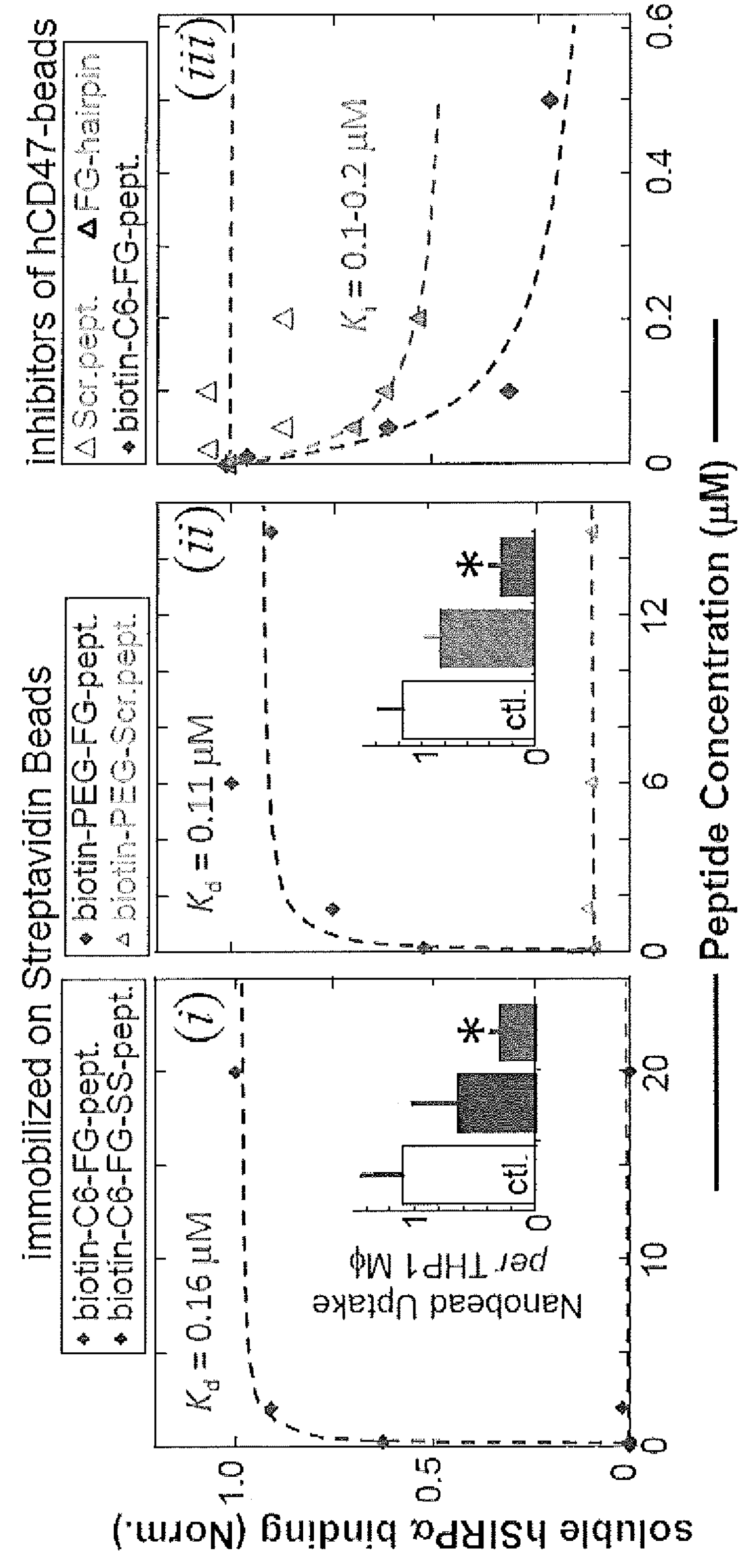
FIG. 4 illustrates binding and phagocytosis inhibition of peptides in relation to human-SIRP-alpha. Affinity of polypeptides coated beads binding to soluble hSIRP-alpha based on flow cytometry. Saturation binding fit gave the indicated dissociation constant, Kd. The insert shows phagocytosis assay in THP-1 cell line in vitro of the different polypeptides designed and coated to Streptavidin polystyrene.

Synthesis of the three designs and Scrambled-peptides with or without biotin attached via either an aminohexanoic acid linker (C6) or a PEG linker, enabled functional testing of binding to soluble hSIRP-alpha as well as inhibition of nanobead phagocytosis. The FG-peptide's affinity for SIRP-alpha ($K_d$=0.11-0.16 μM; FIG. 4-*i,ii*) is consistent with full functionality of the peptide both in vivo and in vitro (FIG. 3B, FIG. 3C). In contrast, the disulfide-stapled FG-SS-peptide showed no significant affinity for hSIRP-alpha and no statistically significant inhibition of phagocytosis, thus revealing the importance of flexibility in maintaining the β-hairpin's surface charge distribution. While the PEG linker improves solubility, the choice of linker has little impact on hSIRP-alpha binding, but scrambling the peptide sequence eliminated binding as well as any statistically significant inhibition of phagocytosis (FIG. 4-*ii*). The 10-aa FG-hairpin was synthesized without attachment of biotin for use as a soluble inhibitor of hSIRP-alpha binding to polypeptide beads. In this inhibition assay, the scrambled peptide was again not functional, but the FG-hairpin inhibited interactions and although inhibition was less than with the FG-peptide, a similar $K_i$≈0.1-0.2 μM (FIG. 3B-*iii*) proved consistent with the $K_d$ measured above. While conformational constraints the minimal FG-hairpin combined with the likely lack of a stable structure underscores the utility of at least some backbone flexibility.

In a non-limiting embodiment, the 10-amino acid or 21-amino acid constructs disclosed herein may have a potential application for targeted therapeutics and clinical transplantation. Use of the minimal 10-amino acid construct may avoid species specificity part and avoid rejection of organs or implanted particles (of any size), since it avoids SIRP-alpha polymorphism binding effect. In another embodiment, the FG peptide may be attached to a polymer as a means to achieve drug delivery in vivo.

Example 4

Prolonged Circulation of Particles Improves Perfusion and Imaging of Tumors

Figure 5A:
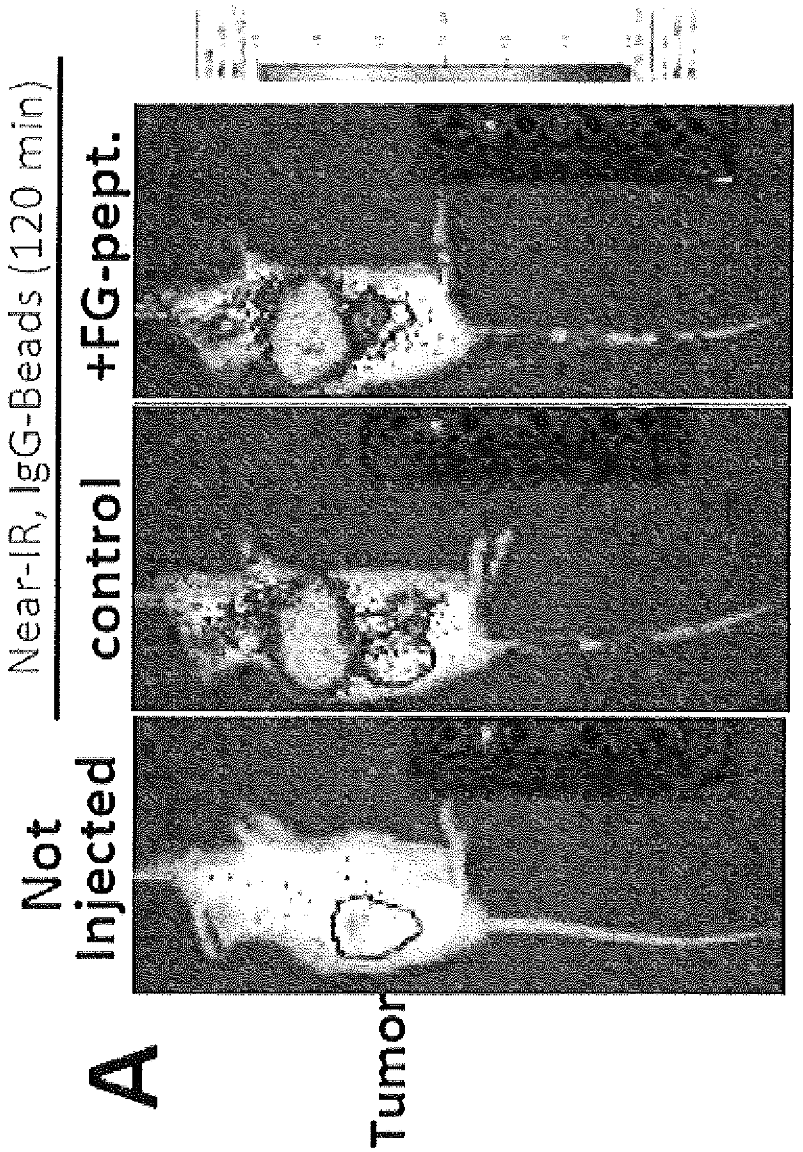
FIGS. 5A-5C, illustrates enhanced tumor imaging. 320 nm streptavidin beads were injected to NSG mice containing A549 tumor cells.

The persistence of FG-beads in blood delayed clearance by the spleen and liver (FIG. 3C) but did not eliminate clearance of particles. Persistent circulation should nonetheless enhance perfusion of organs other than the spleen and liver, and so in order to test this a highly vascularized tissue was imaged with near-infrared fluorescent beads. Subcutaneous tumors were created with human A549 lung epithelial cells xenografted onto the flanks of NSG mice. These cells did not express significant hSIRP-alpha. After injection of the beads into the tail veins, whole body images of live mice were taken periodically starting at 10 min (FIG. 5A).

Figure 5B:
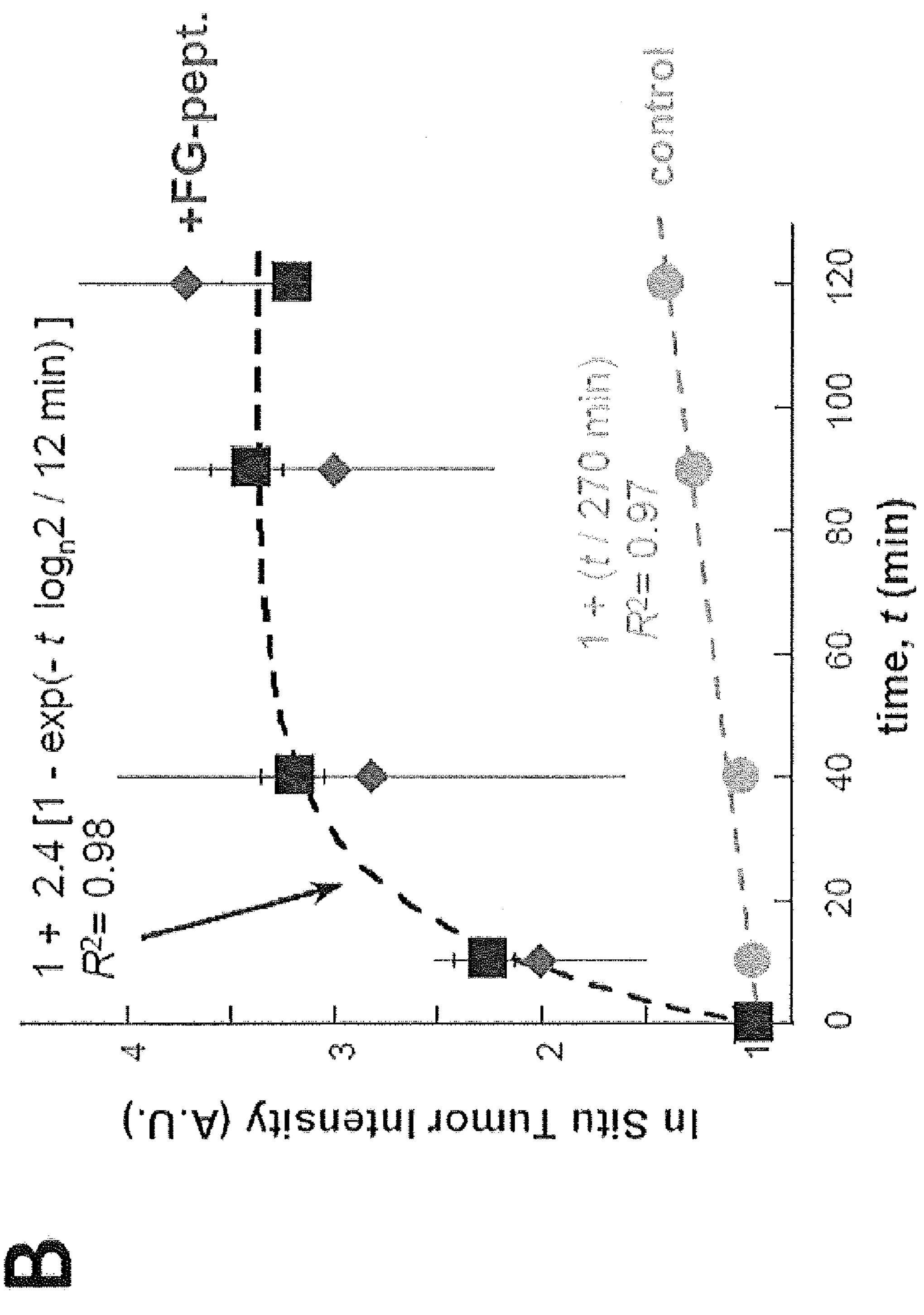
Figure 5C:
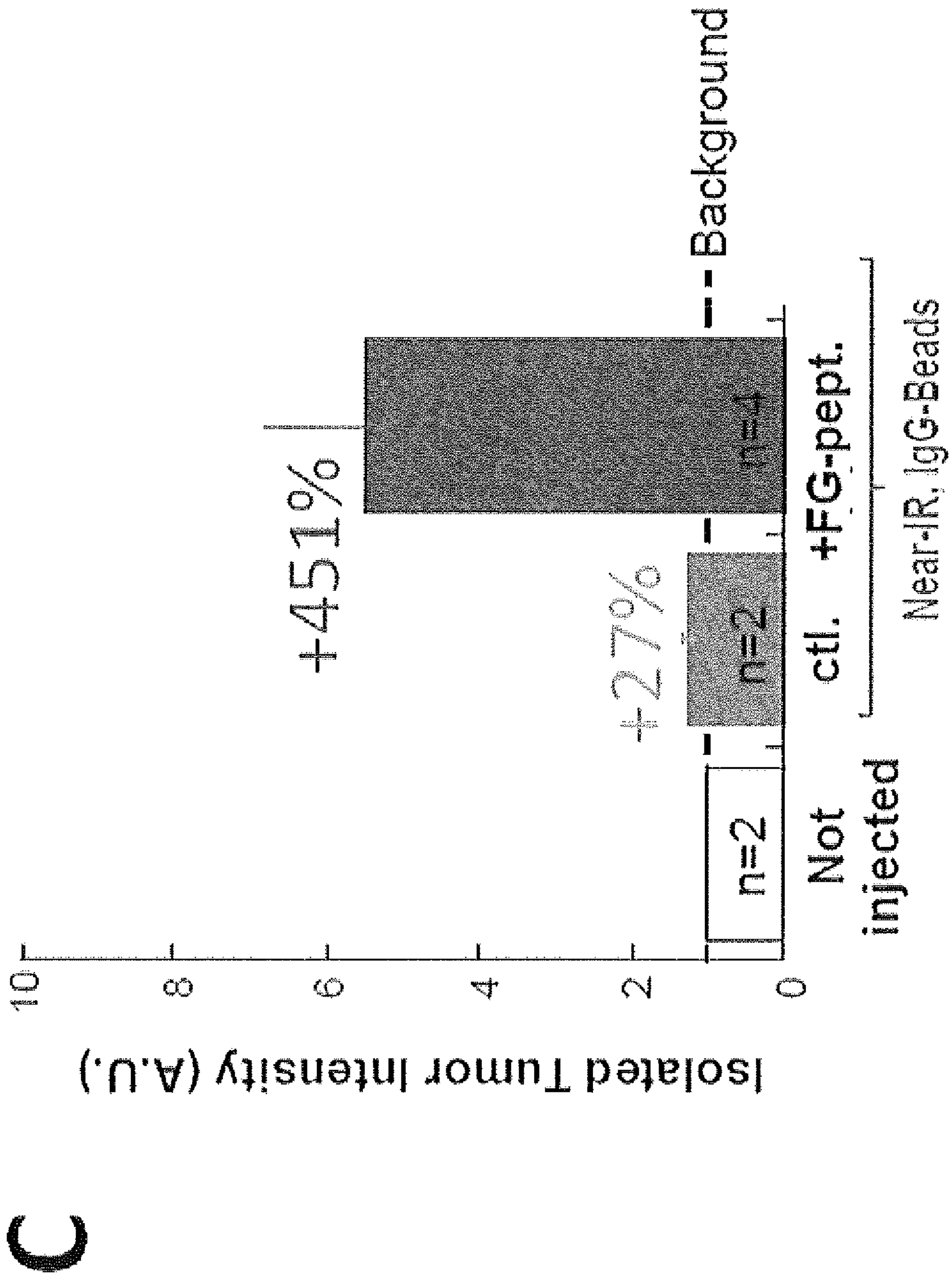

Tumor locations obtained from brightfield imaging allowed an approximate region-of-interest to be defined for in situ fluorescence intensity analysis. As early as 10 min, the FG-beads gave a tumor intensity >2-fold above that of non-injected mice (FIG. 5B) while control beads gave a signal similar to background. With FG-beads, the fluorescence increase fit to first order kinetics, consistent with enhanced perfusion limited by progressive clearance, and the doubling time toward saturation is statistically the same as the relative doubling time for persistent circulation (FIG. 3B). Tumors were subsequently excised and imaged for clearer images that remove background from nearby tissue as well as any uncertainty in the region-of-interest. With FG-beads, the tumors showed 16- to 22-fold enhancement above the near-zero signal with control beads.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A peptide of SEQ ID NO:2, or a salt thereof, wherein:

(i) $Xaa_1$ is Thr; and $Xaa_{12}$ is selected from the group consisting of Thr and null, or (ii) $Xaa_1$ is selected from the group consisting of Cys, Thr and null; and $Xaa_{12}$ is Cys.

2. The peptide of claim 1, or a salt thereof, wherein $Xaa_1$ is Thr and $Xaa_{12}$ is Cys.

3. The peptide of claim 1, or a salt thereof, wherein $Xaa_1$ is null and $Xaa_{12}$ is Cys.

4. The peptide of claim 1, which consists of SEQ ID NO:4, or a salt thereof.

5. The peptide of claim 1, or a salt thereof, wherein $Xaa_1$ is Thr and $Xaa_{12}$ is Thr.

6. The peptide of claim 1, or a salt thereof, wherein $Xaa_1$ is Thr and $Xaa_{12}$ is null.

7. A composition comprising:

compound (II) or a salt thereof:

(II)

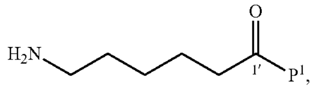

compound (III) or a salt thereof:

(III)

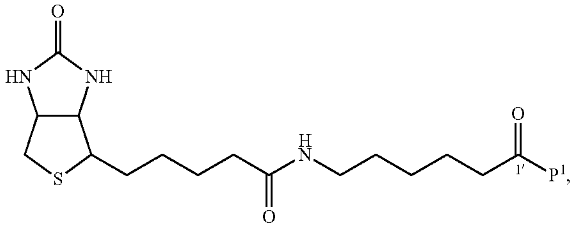

compound (IV) or a salt thereof:

(IV)

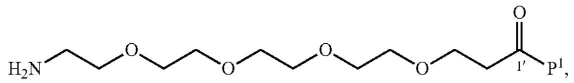

or compound (V) or a salt thereof:

(V)

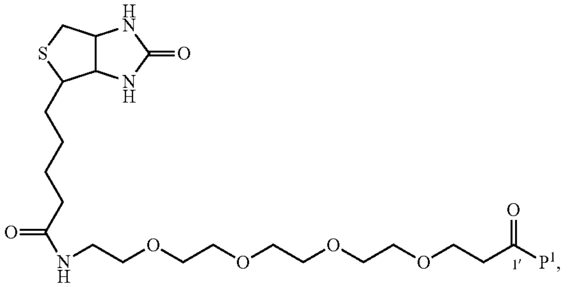

wherein:

$P^1$ comprises a peptide having at least 85% homology with the peptide of SEQ ID NO:2, and $P^1$ is covalently bound through its N-amino terminus via an amide bond to the carbonyl group (1').

8. The composition of claim 7, wherein said $P^1$ comprises a peptide having at least 85% homology with the peptide of SEQ ID NO:3.

9. The composition of claim 7, wherein said $P^1$ comprises a peptide having at least 85% homology with the peptide of SEQ ID NO:4.

10. The composition of claim 7, wherein said $P^1$ comprises a peptide having at least 85% homology with the peptide of SEQ ID NO:1.

11. A composition comprising a chemical agent comprising a compound selected from the group consisting of compounds (II)-(V), wherein said chemical agent is attached to the surface of a solid particle.

12. The composition of claim 11, wherein said solid particle is selected from the group consisting of a nanoparticle, vesicle, dendrimer, engineered cell, tissue fragment, implant, and combinations thereof.

13. The composition of claim 11, further comprising an additional agent selected from the group consisting of a therapeutic agent, imaging agent, radioactive agent, salt, protein, nucleic acid, gas, and combinations thereof, wherein said additional agent is attached to or contained within said solid particle.

14. The composition of claim 11, wherein said chemical agent moiety is attached to said surface of said solid particle by a covalent or non-covalent bond.

15. A method of inhibiting phagocytic activity of at least one phagocyte in a subject, said method comprising administering to said subject a pharmaceutical composition comprising a pharmaceutically effective amount of a peptide-containing moiety or a salt thereof, wherein said peptide-containing moiety comprises a compound selected from the group consisting of:

a peptide of SEQ ID NO:2, wherein: (i) $Xaa_1$ is Thr; and $Xaa_{12}$ is selected from the group consisting of Thr and null, or (ii) $Xaa_1$ is selected from the group consisting of Cys, Thr and null; and $Xaa_{12}$ is Cys;

compound (II):

(II)

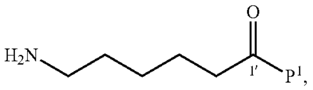

compound (III):

(III)

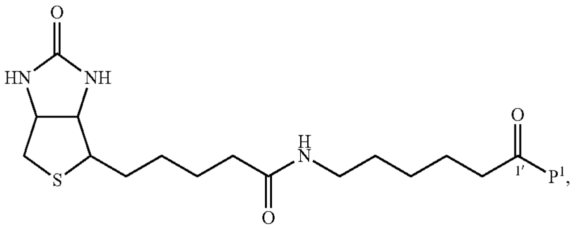

compound (IV):

(IV)

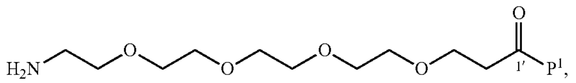

or compound (V):

(V)

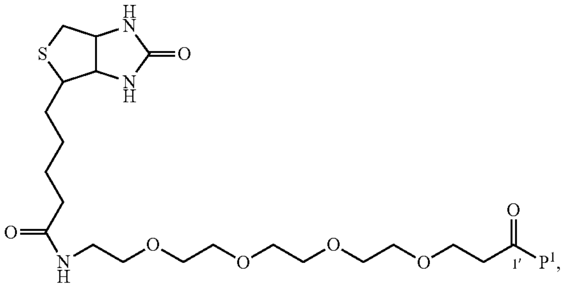

wherein in (II)-(V) $P^1$ comprises a peptide having at least 85% homology with the peptide of SEQ ID NO:2, and is covalently bound through its N-amino terminus via an amide bond to the carbonyl group (1');

whereby administering said composition to said subject inhibits phagocytic activity of said at least one phagocyte in said subject.

16. The method of claim 15, wherein said composition further comprises a solid particle, wherein said peptide-containing moiety is attached to said surface of said solid particle.

17. The method of claim 16, wherein said solid particle is selected from the group consisting of a nanoparticle, vesicle, dendrimer, engineered cell, tissue fragment, implant, and combinations thereof.

18. The method of claim 16, wherein said composition further comprises an agent selected from the group consisting of a therapeutic agent, imaging agent, radioactive agent, salt, protein, nucleic acid, gas, and combinations thereof, wherein said agent is attached to or contained within said solid particle.

19. The method of claim 15, wherein said composition further comprises a conjugated compound covalently linked to said peptide-containing moiety.

20. The method of claim 19, wherein said conjugated compound is selected from the group consisting of a peptide, protein, nucleic acid, lipid, biologically active molecule, and combinations thereof.

21. A method of inhibiting phagocytosis in a subject, said method comprising administering to or introducing into said subject a pharmaceutical composition comprising a peptide-containing moiety or a salt thereof, wherein said peptide-containing moiety comprises a compound selected from the group consisting of:

a peptide of SEQ ID NO:2, wherein: (i) $Xaa_1$ is Thr; and $Xaa_{12}$ is selected from the group consisting of Thr and null, or (ii) $Xaa_1$ is selected from the group consisting of Cys, Thr and null; and $Xaa_{12}$ is Cys;

compound (II):

(II)

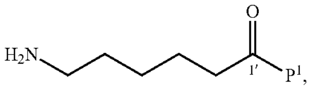

compound (III):

(III)

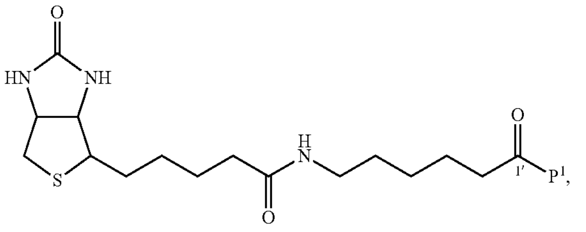

compound (IV):

(IV)

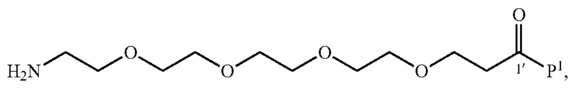

or compound (V):

(V)

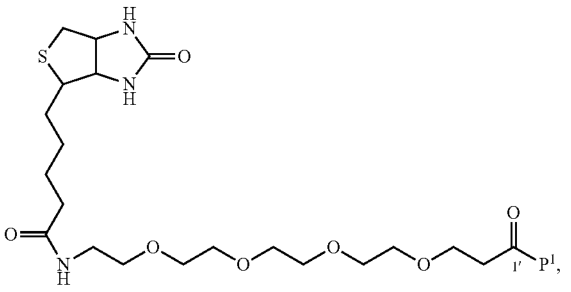

wherein in (II)-(V) $P^1$ comprises a peptide having at least 85% homology with the peptide of SEQ ID NO:2, and is covalently bound through its N-amino terminus via an amide bond to the carbonyl group (1');

whereby said peptide-containing moiety is resistant to phagocytosis in said subject.

22. The method of claim 21, wherein said composition further comprises a solid particle, wherein said peptide-containing moiety is attached to said surface of said solid particle.

23. The method of claim 22, wherein said solid particle is selected from the group consisting of a nanoparticle, vesicle, dendrimer, engineered cell, tissue fragment, implant, and combinations thereof.

24. The method of claim 22, wherein said composition further comprises an agent selected from the group consisting of a therapeutic agent, imaging agent, radioactive agent, salt, protein, nucleic acid, gas and combinations thereof, wherein said agent is attached to or contained within said solid particle.

25. The method of claim 21, wherein said composition further comprises a conjugated compound covalently linked to said peptide-containing moiety.

26. The method of claim 25, wherein said conjugated compound is selected from the group consisting of a peptide, protein, nucleic acid, lipid, biologically active molecule, and combinations thereof.

27. A method of treating or ameliorating an inflammatory disease in a subject, comprising administering to said subject a pharmaceutical composition comprising a pharmaceutically effective amount of a peptide-containing moiety or a salt thereof, wherein said peptide-containing moiety comprises a compound selected from the group consisting of:

a peptide of SEQ ID NO:2, wherein: (i) $Xaa_1$ is Thr; and $Xaa_{12}$ is selected from the group consisting of Thr and null, or (ii) $Xaa_1$ is selected from the group consisting of Cys, Thr and null; and $Xaa_{12}$ is Cys;

compound (II):

(II)

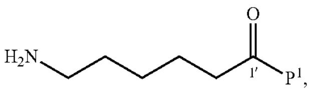

compound (III):

(III)

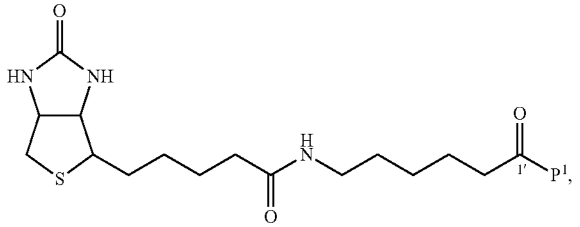

compound (IV):

(IV)

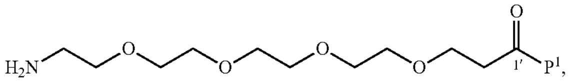

or compound (V):

(V)

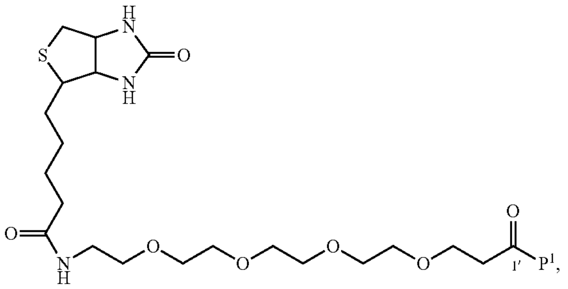

wherein in (II)-(V) $P^1$ comprises a peptide having at least 85% homology with the peptide of SEQ ID NO:2, and is covalently bound through its N-amino terminus via an amide bond to the carbonyl group (1');

whereby administering said composition to said subject treats or ameliorates said inflammatory disease in said subject.

28. The method of claim 27, wherein said composition further comprises a solid particle, wherein said peptide-containing moiety is attached to said surface of said solid particle.

29. The method of claim 28, wherein said solid particle is selected from the group consisting of a nanoparticle, vesicle, dendrimer, engineered cell, tissue fragment, implant, and combinations thereof.

30. The method of claim 28, wherein said composition further comprises an agent selected from the group consisting of a therapeutic agent, imaging agent, radioactive agent, salt, protein, nucleic acid, gas, and combinations thereof, wherein said agent is attached to or contained within said solid particle.

31. The method of claim 27, wherein said composition further comprises a conjugated compound covalently linked to said peptide-containing moiety.

32. The method of claim 31, wherein said conjugated compound is selected from the group consisting of a peptide, protein, nucleic acid, lipid, biologically active molecule, and combinations thereof.

* * * * *